(12) United States Patent
Fors et al.

(10) Patent No.: US 7,574,030 B2
(45) Date of Patent: Aug. 11, 2009

(54) AUTOMATED DIGITIZED FILM SLICING AND REGISTRATION TOOL

(75) Inventors: Steven Lawrence Fors, Chicago, IL (US); Charles Cameron Brackett, Overland Park, KS (US); Mark M. Morita, Arlington Heights, IL (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 1120 days.

(21) Appl. No.: 10/723,790

(22) Filed: Nov. 26, 2003

(65) Prior Publication Data

US 2005/0111733 A1 May 26, 2005

(51) Int. Cl.
*G06K 9/34* (2006.01)
*H04N 1/04* (2006.01)

(52) U.S. Cl. .................. 382/131; 382/132; 382/173; 358/487

(58) Field of Classification Search .......... 382/128, 382/131, 132, 173; 358/450, 487
See application file for complete search history.

(56) References Cited

U.S. PATENT DOCUMENTS

| | | | | |
|---|---|---|---|---|
| 4,829,181 A * | 5/1989 | Shimura | ............ | 250/584 |
| 4,847,694 A * | 7/1989 | Nishihara | ............ | 358/434 |
| 5,241,472 A * | 8/1993 | Gur et al. | ............ | 382/128 |
| 5,337,164 A * | 8/1994 | Yabe et al. | ............ | 358/487 |
| 5,440,403 A * | 8/1995 | Hashimoto et al. | ............ | 358/444 |
| 5,452,416 A * | 9/1995 | Hilton et al. | ............ | 715/783 |
| 5,586,262 A * | 12/1996 | Komatsu et al. | ............ | 705/2 |
| 5,777,753 A * | 7/1998 | McShane et al. | ............ | 358/302 |
| 5,850,297 A * | 12/1998 | Honda | ............ | 358/474 |
| 5,859,891 A * | 1/1999 | Hibbard | ............ | 378/62 |
| 5,892,840 A * | 4/1999 | Jang et al. | ............ | 382/132 |
| 5,986,773 A * | 11/1999 | Goto et al. | ............ | 358/487 |
| 6,212,291 B1 * | 4/2001 | Wang et al. | ............ | 382/132 |
| 6,272,470 B1 * | 8/2001 | Teshima | ............ | 705/3 |
| 6,339,485 B1 * | 1/2002 | Yamada | ............ | 358/504 |
| 6,346,998 B2 * | 2/2002 | Shiota et al. | ............ | 358/487 |
| 6,421,079 B1 * | 7/2002 | Truc et al. | ............ | 348/96 |
| 6,427,058 B1 * | 7/2002 | Akiba et al. | ............ | 399/82 |
| 6,559,967 B1 * | 5/2003 | Akiba et al. | ............ | 358/1.16 |
| 6,574,629 B1 * | 6/2003 | Cooke, Jr. et al. | ............ | 707/10 |
| 6,754,375 B1 * | 6/2004 | Noblett et al. | ............ | 382/129 |
| 6,856,422 B1 * | 2/2005 | Higashibata et al. | ............ | 358/1.18 |
| 6,904,161 B1 * | 6/2005 | Becker et al. | ............ | 382/128 |
| 6,917,826 B2 * | 7/2005 | Wei et al. | ............ | 600/407 |
| 6,947,584 B1 * | 9/2005 | Avila et al. | ............ | 382/131 |
| 6,999,558 B2 * | 2/2006 | Okoda | ............ | 378/102 |
| 7,146,031 B1 * | 12/2006 | Hartman et al. | ............ | 382/132 |
| 2004/0161139 A1 * | 8/2004 | Samara et al. | ............ | 382/131 |
| 2004/0218790 A1 * | 11/2004 | Ping Lo | ............ | 382/124 |
| 2005/0063584 A1 * | 3/2005 | Guo | ............ | 382/162 |

* cited by examiner

*Primary Examiner*—Brian P Werner
*Assistant Examiner*—Anthony Mackowey
(74) *Attorney, Agent, or Firm*—Fletcher Yoder

(57) ABSTRACT

Film-based images can be scanned in a conventional manner, then digitally designated and "cut" from the digital file resulting from the scan. These selected images can then be collated and registered as individual images, or slices in certain contexts, allowing them to be assembled in various presentations, such as in stack mode with digitally-acquired images. The resulting collated files can then be stored by the user as a new series of images. The technique thus greatly facilitates the access and comparison of the images regardless of the originating medium.

32 Claims, 8 Drawing Sheets

AUTOMATED DIGITIZED FILM SLICING AND REGISTRATION TOOL

BACKGROUND OF THE INVENTION

The present invention relates generally to imaging systems, such as systems used to present images digitally that are acquired through various different techniques. In particular, the invention relates to the presentation of images from different media, such as film-based images for presentation and comparison to one another and to images acquired through digital media.

Image acquisition and comparison are fundamental processes in many areas. In the medical diagnostics field, for example, anatomical images have been produced through many different techniques and modalities. Very conventional modalities include X-ray imaging systems which traditionally produced film that could be easily reproduced and displayed in very high quality reproductions for reading by a clinician or radiologist. Increasingly, however, such fields have moved towards digital imaging. Digital imaging provides significant advantages, including the ease of storage and transmission of images for display and analysis. Such images can also be manipulated in very effective and efficient manners, such as to display images side-by-side or in sequences that make their understanding and analysis much more effective.

Problems have arisen, however, in the comparison of images resulting from different types of systems. For example, conventional film-based systems, such as X-ray systems, will continue to be used in many settings due to their simplicity and robustness, and due to the fact that they are well understood and well established. However, integrating images produced on such systems with digital systems has been a challenge. Traditionally, the films are scanned to produce digital data, and the digital data is stored for transmission and display. However, the only displays that have been available for such scanned film have been so-called "sheet modes" on various types of workstations. For example, picture archiving and communication systems (PACS) can display such images in sheet mode, with the display effectively resembling the sheet of film from which the data originated. Powerful tools of the PACS workstations, however, are unavailable or useless on such images due to the relatively rigid nature of the image data file. By comparison, radiologists can read digitally-acquired images, as from CT and MR studies in stack mode, wherein different images, such as images acquired at different points in time, can be displayed together. The comparison of such digitally-acquired images with sheet mode displays of scanned film-based images is quite inefficient and difficult, and results in time-consuming consideration of one or the other of the image sets.

An improved technique is needed for enhancing the efficiency and facility of reading images from different originating media, particularly images from film and images from digital acquisition systems. There is a particular need at present for a system which can facilitate the integration of both film-based and digitally-acquired images in the medical diagnostics field.

BRIEF DESCRIPTION OF THE INVENTION

The present invention provides a novel technique designed to address such needs. In accordance with the technique, film-based images can be scanned in a conventional manner, then digitally designated and "cut" from the digital file resulting from the scan. These selected images can then be collated and registered as individual images, or slices in certain contexts, allowing them to be assembled in various presentations, such as in stack mode with digitally-acquired images. The resulting collated files can then be stored by the user as a new series of images. The technique thus greatly facilitates the access and comparison of the images regardless of the originating medium.

For example, the technique provides a method for processing digitized images that may include accessing a digitized sheet of a number of digitized images scanned from an analog sheet of film supporting an analog image, configuring a template based on properties of the analog and digitized image to process the digitized images, and outlining and cutting the digitized image with the template to produce processed digitized image data comprising separated digitized images. The template configuration generally corresponds to the number and size of the analog or digitized images. The template may be placed over the digitized sheet to cut and separate one or more digitized images or placed in the template to cut and separate the digitized images. The processed digitized image data and individual images may be stored and displayed on a PACS workstation monitor, collated, compared, and/or registered.

The separated digitized images may be displayed in at least one of a cine serial display, a composite, an overlay, and a stack mode. Aspects of the technique may further include comparing or registering one or more of the separated digitized images with related digital images. The analog images may be originally reproduced on the analog sheet of film from image data digitally-acquired by at least one of a magnetic resonance imaging (MRI) system, a computed tomography (CT) imaging, and a digital X-ray imaging system, as well as from other imaging modalities. Moreover, the sheet of film may support images originally acquired with a conventional X-ray imaging system.

Advantageously, aspects of the technique provide for a system for processing a scanned image file of a conventional sheet of film. An imaging system, such as a conventional X-ray imaging system, a digital X-ray imaging system, a CT imaging system, an MR imaging system, or other imaging modality, may acquire image data and a sheet of film supporting the resulting images may be produced. One or more of the images on the film is then digitized. The technique provides for an interface for accessing, displaying, reviewing, and processing the digitized sheet of film, and a storage for storing image data of the processed digitized sheet of film. Processing of the digitized sheet of film may include cropping and registering individual digitized images within the digitized sheet of film, and storing image data of the cropped digitized images. The system may also include a second interface for displaying the stored image data of the cropped digitized images in cine serial mode, stack mode, as an overlay or composite, and so forth. The system may include yet another interface for comparing the cropped digitized images with digitally-acquired images. Moreover, the system may include an analog-to-digital device or scanner for converting analog film images to digitized images.

Finally, in accordance with aspects of the technique, a digitized image file may include image data of designated digitized images cut and copied from a digitized sheet of analog images scanned from a conventional analog sheet of film in sheet mode. The digitized sheet of film may be cut with a digital template configured based on properties of the analog and digitized images. Moreover, the digitized sheet of analog images may have been scanned from an analog sheet of film reproduced from image data acquired with at least one of a magnetic resonance imaging (MRI) system, a computed tomography (CT) imaging, an X-ray imaging system, or any other suitable imaging system or modality.

DETAILED DESCRIPTION OF SPECIFIC EMBODIMENTS

Figure 1:
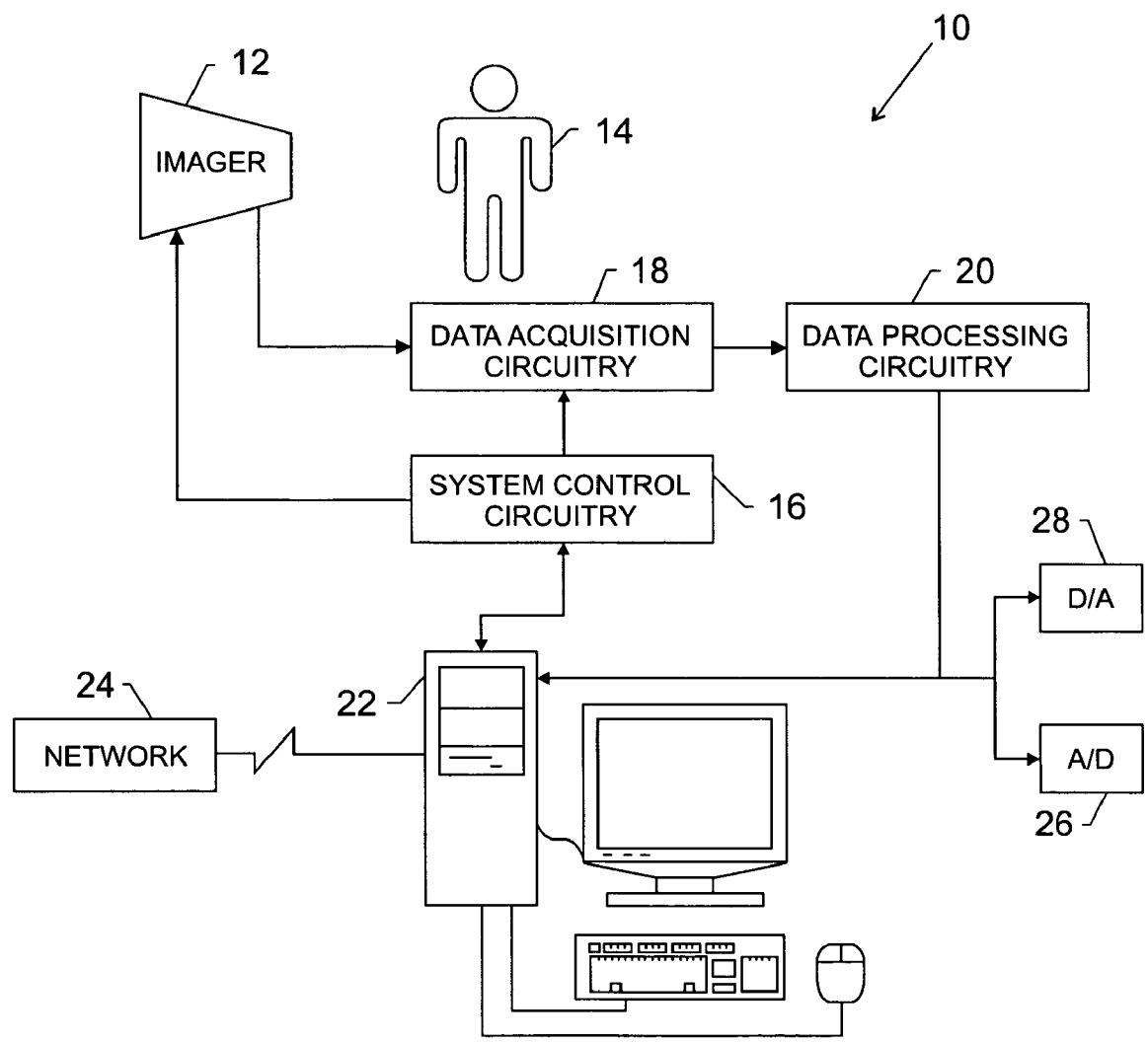
FIG. 1 is a general diagrammatical representation of certain functional components of an exemplary image data-producing system, in the form of a medical diagnostic imaging system.

Image studies often involve a comparison of several images or series of images, and involve media that may be film-based or digital. For film-based images, radiologists and other physicians may typically read analog sheets of film in a light box. To avoid problems such as light emanating from the light box into the room, as well as to avoid limitations on analog storage, retrieval, and processing, the film-based images may be digitize by scanning the sheets of film. The digitized images may be displayed and viewed, for example, on a PACS workstation monitor, and provide for more efficient electronic storage, retrieval, and processing. Digitization also greatly facilitates transmission and sharing of images for review by others, such as specialists. However, where an entire sheet has been scanned, the digitized image data are typically resistant to further processing and cannot be viewed, for example, in useful stack modes, and other views.

In response, aspects of the present technique provide for a digital template or algorithm to select the digitized images from the digitized sheet to compare and stack the individual digitized images with each other and with other related images, such as those digitally-acquired in a different temporal session. The exemplary digital template application may be manual or semi-automated, or instead, a template algorithm, for example, may be fully automated to recognize the properties of the digitized sheet and to automatically cut the digitized images within the digitized sheet. In general, the technique allows for joining and combining of images and various image series in many ways, such as viewing the images in stack mode to "cine" through the images. Such a "cine" review may, for example, aid in viewing and evaluating a change of anatomy in the stacked images or image series.

In one embodiment, after the conventional sheet film has been scanned and stored as digitized sheet film, a clinician may access and display the scanned image file, which in a medical diagnostic context may conform to a standard Digital Imaging and Communications in Medicine (DICOM) format. The clinician may, for example, outline and copy portions of the image file, such as the individual digitized images within the digitized sheet, and place the portions in a separate file, adjusting the order of the individual images as desired. The outlining and coping of the individual images may be accomplished, for example, by placing the digitized sheet in the digital template or placing a digital template over the digitized sheet. Additionally, in the separate file, a DICOM header, for example, may define the image series and the order of the images. The DICOM standard promotes a generic communication method for heterogeneous imaging systems, allowing the transfer of images and associated information. Other standard presentations may, of course, be used, particularly in different imaging fields and applications.

It should be noted that while reference is made in the present discussion to medical diagnostic images, the present invention is not limited to such applications. Rather, the techniques may find application in a wide range of imaging fields, including photographic imaging, part and parcel inspection, and so forth, where inspection of film-based images would be facilitated by digitization and manipulation, and particularly where comparison of such images with digitally-acquired images would be useful.

In the acquisition of the images, various imaging resources may be available. For example, in the medical field, for diagnosing medical events and conditions in both soft and hard tissue, and for analyzing features and function of specific anatomies, such medical imaging resources or systems may incorporate modalities such as X-ray, Computed Tomography (CT), Magnetic Resonance Imaging (MRI), Positron Emission Tomography (PET), thermoacoustic imaging, optical imaging, nuclear medicine-based imaging, and so forth. FIG. 1 depicts an overview of an imaging system 10, which may be representative of a variety of imaging modalities. An imaging system 10 generally includes some type of imager 12 which detects signals and converts the signals to useful data. As described more fully below, the imager 12 may operate in accordance with various physical principles for creating the image data. In general, however, in image data indicative of regions of interest in a patient 14 are created by the imager either in a conventional support, such as photographic film, or in a digital medium.

The imager 12 operates under the control of system control circuitry 16. The system control circuitry may include a wide range of circuits, such as radiation source control circuits, timing circuits, circuits for coordinating data acquisition in conjunction with patient or table of movements, circuits for controlling the position of radiation or other sources and of detectors, and so forth. The imager 12, following acquisition of the image data or signals, may process the signals, such as for conversion to digital values, and forwards the image data to data acquisition circuitry 18.

In the case of analog media, such as photographic film, the data acquisition system may generally include supports for the film, as well as equipment for developing the film and producing hardcopies that may be subsequently digitized. For digital systems, the data acquisition circuitry 18 may perform a wide range of initial processing functions, such as adjustment of digital dynamic ranges, smoothing or sharpening of data, as well as compiling of data streams and files, where desired. The data are then transferred to data processing circuitry 20 where additional processing and analysis are performed. For conventional media such as photographic film, the data processing system may apply textual information to films, as well as attach certain notes or patient-identifying information. For the various digital imaging systems available, the data processing circuitry 20 may perform substantial analyses of data, ordering of data, sharpening, smoothing, feature recognition, and so forth.

Ultimately, the image data are forwarded to some type of operator interface 22 for viewing and analysis. While operations may be performed on the image data prior to viewing, the operator interface 22 is at some point useful for viewing reconstructed images based upon the image data collected. It should be noted that in the case of photographic film, images are typically posted on light boxes or similar displays to permit radiologists and attending physicians to more easily read and annotate image sequences. The images may also be stored in short or long-term storage devices, for the present purposes generally considered to be included within the interface 22, such as picture archiving communication systems. The image data can also be transferred to remote locations, such as via a network 24. It should also be noted that, from a general standpoint, the operator interface 22 affords control of the imaging system, typically through interface with the system control circuitry 16. Moreover, it should also be noted that more than a single operator interface 22 may be provided. Accordingly, an imaging scanner or station may include an interface which permits regulation of the parameters involved in the image data acquisition procedure, whereas a different operator interface may be provided for manipulating, enhancing, and viewing resulting reconstructed images.

In some circumstances, images acquired on conventional media, such as photographic film, may be converted to digitized images via an analog-to-digital converter 26, such as a digitizer, scanner, and the like. These digitized images or files may be digitally stored locally at the operator interface 22 or at other memory locations via network 24. It should be noted that handling of digitized images may differ from the handling of digitally acquired images due to, for example, software limitations with digitized images. It is typical, for example, for conventional film to be scanned in the sheet mode, a digitized format that is unfortunately more resistant to handling and processing than the typical digital (digitally-acquired) format.

Furthermore, images originally acquired in the form of digital media are often printed or reproduced on film for review and storage. Historically, the quality of conventional film images and physician preference, as well as problems with digital images, such as lack of appropriate digital image viewing stations, the lack of digital storage capacity, and so forth, often resulted in medical images that are digitally acquired, such as by an MRI system or CT system, to be produced on conventional high-quality film for review and storage. In many situations, due to the excellent contrast and readability of film, radiologists and other reviewers may simply prefer the use of film for review and analysis. Though conventional analog film has remain the medium of choice in many applications, as the availability and quality of digital display stations, storage capability, image handling and processing, have improved, the storing and direct review of digital and digitized images are becoming increasingly prevalent. A problem is that digitized images may not compare well with digitally-acquired images and may escape valuable digital handling capabilities.

To discuss the technique in greater detail, two specific medical imaging modalities based upon the overall system architecture outlined in FIG. 1 are discussed below. The two modalities, magnetic resonance imaging (MRI) and computed tomography (CT) imaging, may be used, for example, to digitally-acquire image data and reproduce the image data in sheet mode on conventional analog film. The two modalities are given only as examples, and it should be apparent that the present technique may apply to a variety of imaging modalities and applications.

Figure 2:
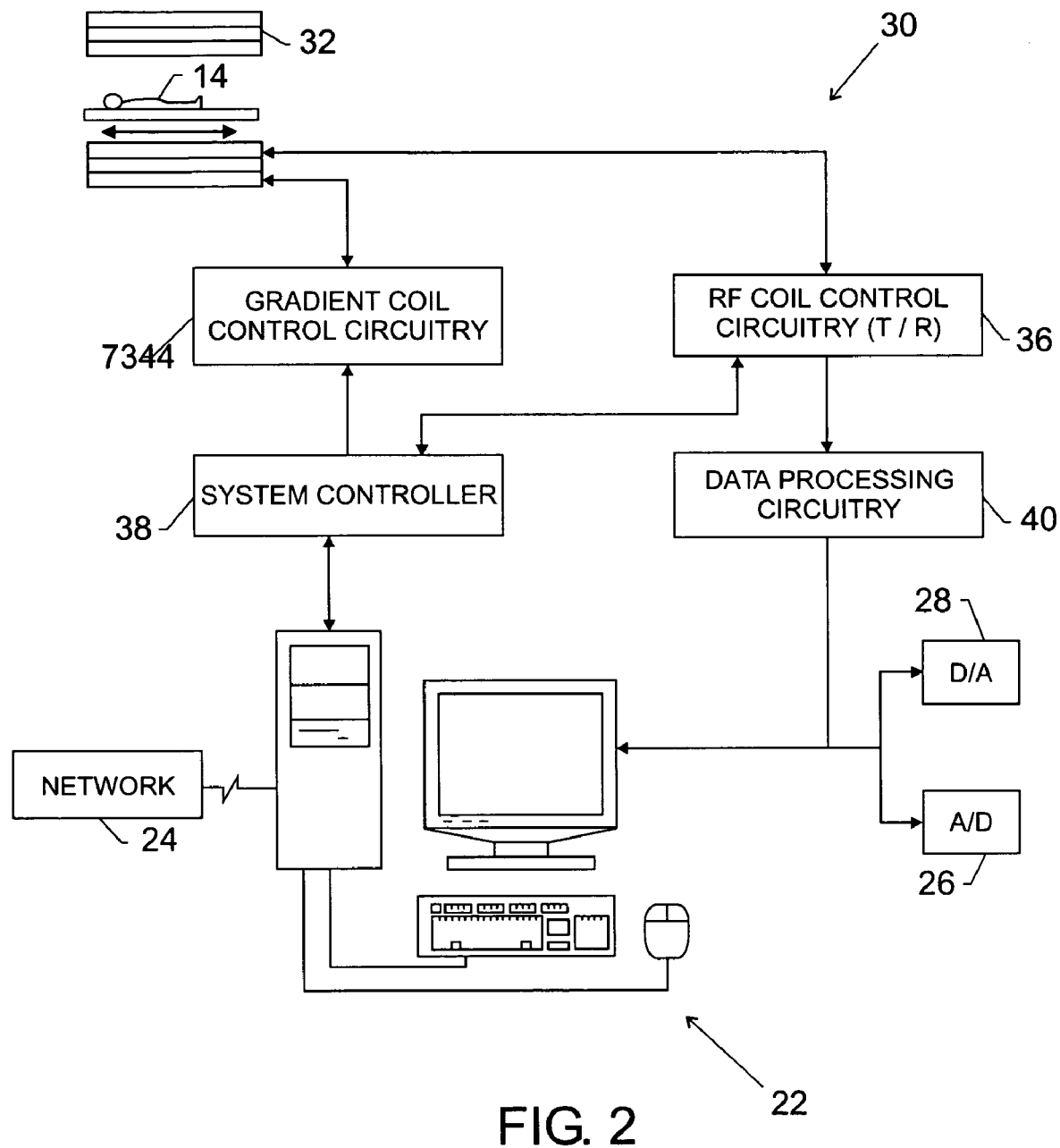
FIG. 2 is a diagrammatical representation of a particular imaging system of the type shown in FIG. 1, in this case an exemplary magnetic resonance (MR) imaging system.

FIG. 2 represents a general diagrammatical representation of a magnetic resonance imaging system 30. The system includes a scanner 32 in which a patient 14 is positioned for acquisition of image data. The scanner 32 generally includes a primary magnet for generating a magnetic field which influences gyromagnetic materials within the patient's body. As the gyromagnetic material, typically water and metabolites, attempts to align with the magnetic field, gradient coils produce additional magnetic fields which are orthogonally oriented with respect to one another. The gradient fields effectively select a slice of tissue through the patient for imaging, and encode the gyromagnetic materials within the slice in accordance with phase and frequency of their rotation. A radio-frequency (RF) coil in the scanner generates high frequency pulses to excite the gyromagnetic material and, as the material attempts to realign itself with the magnetic fields, magnetic resonance signals are emitted which are collected by the radio-frequency coil.

The scanner 32 is coupled to gradient coil control circuitry 34 and to RF coil control circuitry 36. The gradient coil control circuitry permits regulation of various pulse sequences which define imaging or examination methodologies used to generate the image data. Pulse sequence descriptions implemented via the gradient coil control circuitry 34 are designed to image specific slices, anatomies, as well as to permit specific imaging of moving tissue, such as blood, and defusing materials. The pulse sequences may allow for imaging of multiple slices sequentially, such as for analysis of various organs or features, as well as for three-dimensional image reconstruction. The RF coil control circuitry 36 permits application of pulses to the RF excitation coil, and serves to receive and partially process the resulting detected MR signals. It should also be noted that a range of RF coil structures may be employed for specific anatomies and purposes. In addition, a single RF coil may be used for transmission of the RF pulses, with a different coil serving to receive the resulting signals.

The gradient and RF coil control circuitry function under the direction of a system controller 38. The system controller implements pulse sequence descriptions which define the image data acquisition process. The system controller will generally permit some amount of adaptation or configuration of the examination sequence by means of an operator interface 22.

Data processing circuitry 40 receives the detected MR signals and processes the signals to obtain data for reconstruction. In general, the data processing circuitry 40 digitizes the received signals, and performs a two-dimensional fast Fourier transform on the signals to decode specific locations in the selected slice from which the MR signals originated. The resulting information provides an indication of the intensity of MR signals originating at various locations or volume elements (voxels) in the slice. Each voxel may then be converted to a pixel intensity in image data for reconstruction. The data processing circuitry 40 may perform a wide range of other functions, such as for image enhancement, dynamic range adjustment, intensity adjustments, smoothing, sharpening, and so forth. The resulting processed image data is typically forwarded to an operator interface for viewing, as well as to short or long-term storage. As in the case of foregoing imaging systems, MR image data may be viewed locally at a scanner location, or may be transmitted to remote locations both within an institution and remote from an institution such as via network 24.

Figure 3:
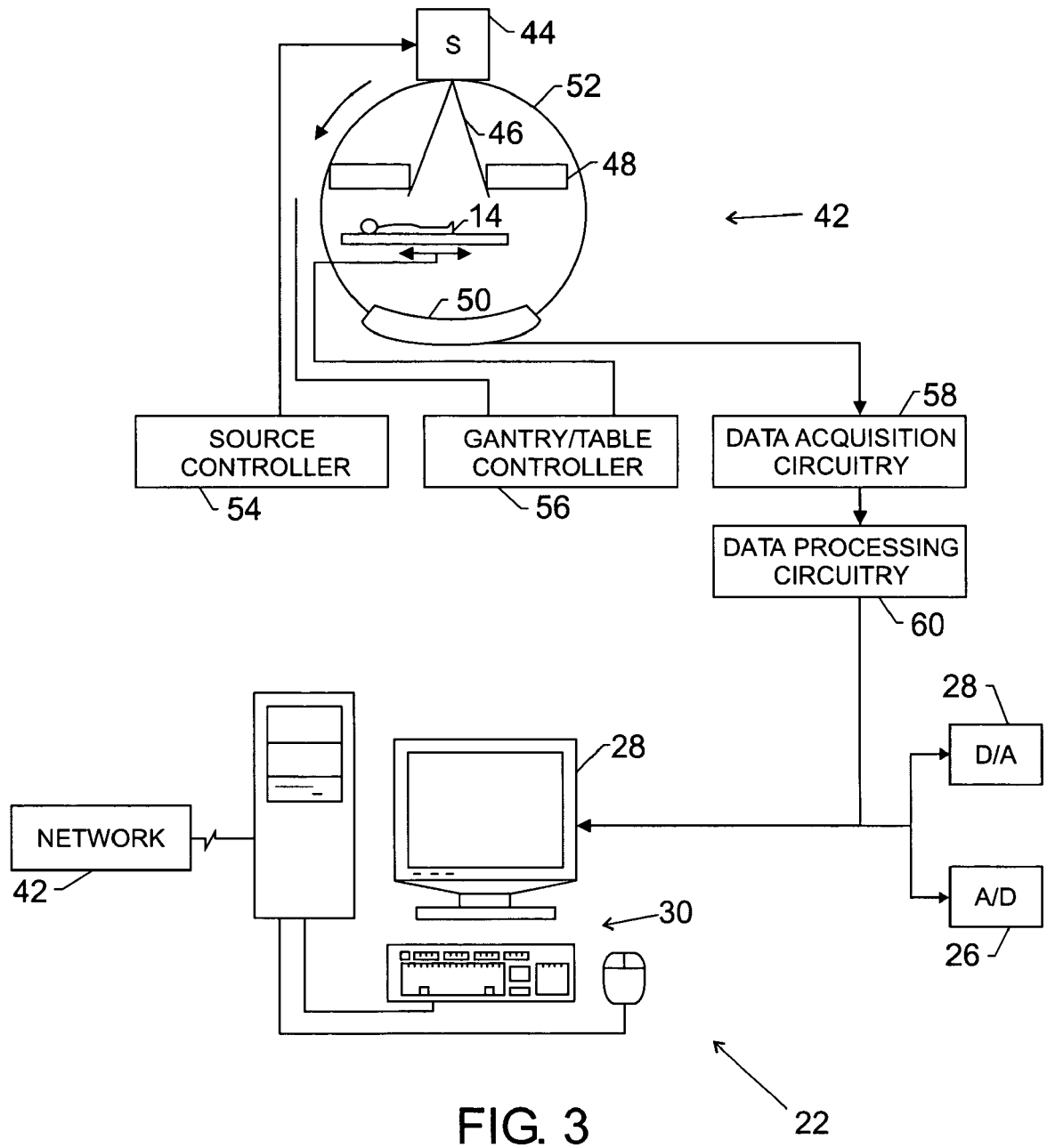
FIG. 3 is a diagrammatical representation of a particular imaging system of the type shown in FIG. 1, in this case an exemplary computed tomography (CT) imaging system.

FIG. 3 illustrates the basic components of a computed tomography (CT) imaging system. The CT imaging system 42 includes a radiation source 44 which is configured to generate X-ray radiation in a fan-shaped beam 46. A collimator 48 defines limits of the radiation beam. The radiation beam 46 is directed toward a curved detector 50 made up of an array of photodiodes and transistors which permit readout of charges of the diodes depleted by impact of the radiation from the source 44. The radiation source, the collimator and the detector are mounted on a rotating gantry 52 which enables them to be rapidly rotated (such as at speeds of two rotations per second).

During an examination sequence, as the source and detector are rotated, a series of view frames are generated at angularly-displaced locations around a patient 14 positioned within the gantry. A number of view frames (e.g. between 500 and 1000) are collected for each rotation, and a number of rotations may be made, such as in a helical pattern as the patient is slowly moved along the axial direction of the system. For each view frame, data is collected from individual pixel locations of the detector to generate a large volume of discrete data. A source controller 54 regulates operation of the radiation source 44, while a gantry/table controller 56 regulates rotation of the gantry and control of movement of the patient.

Data collected by the detector is digitized and forwarded to a data acquisition circuitry 58. The data acquisition circuitry may perform initial processing of the data, such as for generation of a data file. The data file may incorporate other useful information, such as relating to cardiac cycles, positions within the system at specific times, and so forth. Data processing circuitry 60 then receives the data and performs a wide range of data manipulation and computations.

In general, data from the CT scanner can be reconstructed in a range of manners. For example, view frames for a full 360° of rotation may be used to construct an image of a slice or slab through the patient. However, because some of the information is typically redundant (imaging the same anatomies on opposite sides of a patient), reduced data sets comprising information for view frames acquired over 180° plus the angle of the radiation fan may be constructed. Alternatively, multi-sector reconstructions are utilized in which the same number of view frames may be acquired from portions of multiple rotational cycles around the patient. Reconstruction of the data into useful images then includes computations of projections of radiation on the detector and identification of relative attenuations of the data by specific locations in the patient. The raw, the partially processed, and the fully processed data may be forwarded for post-processing, storage and image reconstruction. The data may be available immediately to an operator, such as at an operator interface 22, and may be transmitted remotely via network 24.

For imaging systems, such as the CT and MRI systems discussed above, the present technique enhances the efficiency and capability of reading images from different originating media, particularly images from film and images from digitally-acquired systems. The technique provides for a system which can facilitate the integration of both film-based and digitally-acquired images in the medical diagnostics field, as well as in any other field of use. In accordance with the technique, film-based images can be scanned in a conventional manner, then digitally designated and "cut" from the digital file resulting from the scan. These selected images can then be collated and registered as individual images or slices, and assembled in various presentations, such as in stack mode with digitally-acquired images. The resulting collated files can then be stored by the user as a new series of images. The technique thus greatly facilitates the access and comparison of the images regardless of the originating medium.

For example, with the technique, the powerful tools of the picture archiving and communication systems (PACS) workstations are made available to scanned film-based images. The relatively rigid nature of such image data is overcome. The PACS, once limited to displaying such digitized images in sheet mode, with the display effectively resembling the sheet of film from which the data originated, can now handle such image data in the same way users can read digitally-acquired images, as from CT and MR studies in stack mode, wherein different images, such as images acquired at different points in time, can be displayed together. Registration and other tools in the PAC tools set, such as linking, cine, and so forth, are made available to the image data processed and copied from digitized image files of scanned films that previously could only be displayed in sheet mode. The facilitated comparison of digitally-acquired images with cut images from the sheet mode displays saves time and improves image analysis and efficiency. Aspects of the technique and a picture archive and communication system (PACS) are discussed in more detail below.

Figure 4:
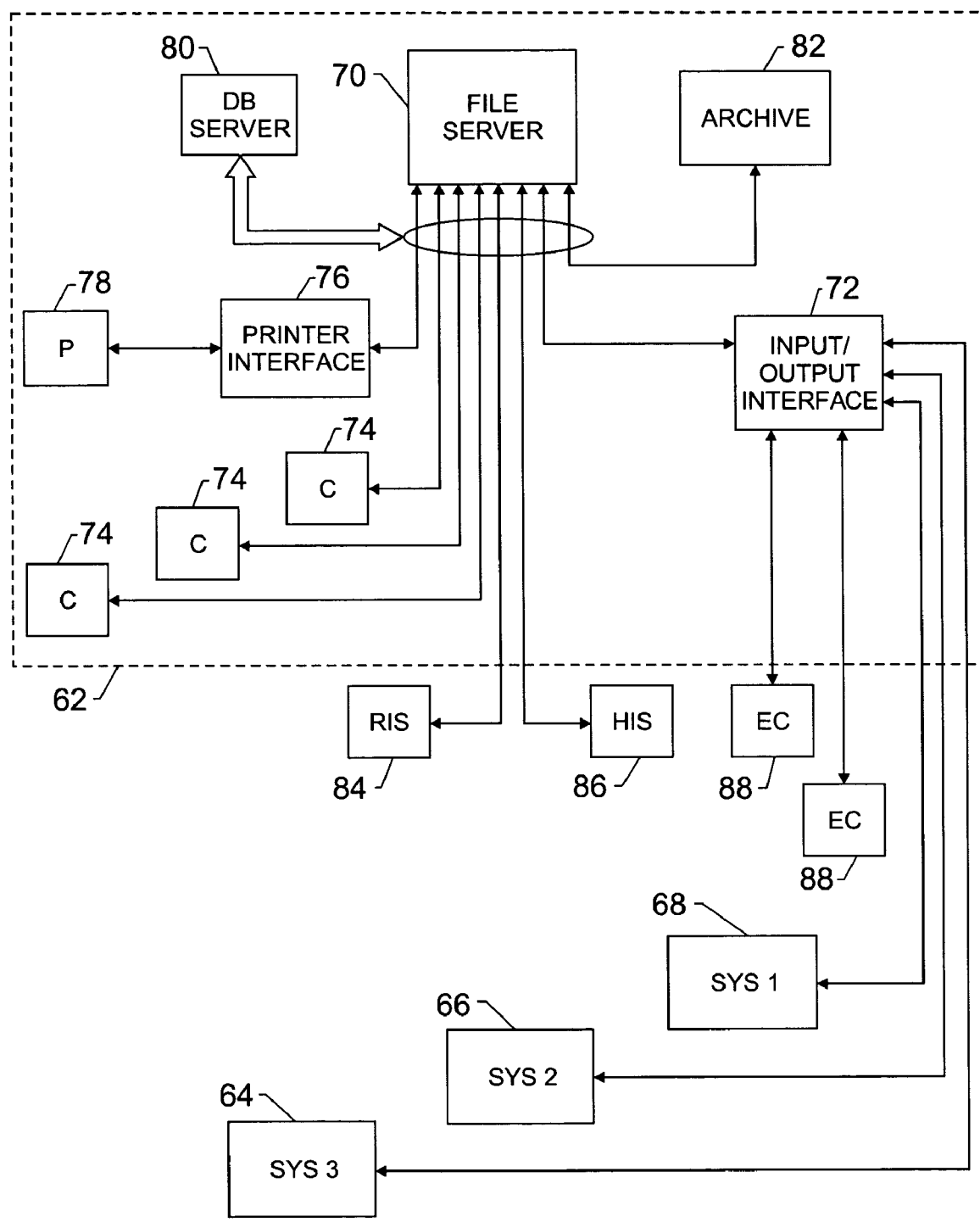
FIG. 4 is a diagrammatical representation of an exemplary image management system, in the illustrated example a picture archiving and communication system or PACS, for receiving, storing, and reading image data.

FIG. 4 illustrates an exemplary image data management system in the form of a PACS 62 for receiving, processing, and storing image data. In the illustrated embodiment, PACS 62 receives image data from several separate imaging systems designated by reference numerals 64, 66 and 68. As will be appreciated by those skilled in the art, the imaging systems may be of the various types and modalities previously discussed, such as magnetic resonance imaging (MRI) systems, computed tomography (CT) systems, positron emission tomography (PET) systems, radio fluoroscopy (RF), computed radiography (CR), ultrasound systems, and so forth. Moreover, as previously noted, the systems may include processing stations or digitizing stations, such as equipment designed to provide digitized image data based upon existing film or hard copy images. It should also be noted that the systems supplying the image data to the PACS may be located locally with respect to the PACS, such as in the same institution or facility, or may be entirely remote from the PACS, such as in an outlying clinic or affiliated institution. In the latter case, the image data may be transmitted via any suitable network link, including open networks, proprietary networks, virtual private networks, and so forth.

PACS 62 includes one or more file servers 70 designed to receive, process, and/or store image data, and to make the image data available for further processing and review. Server 70 receives the image data through an input/output interface 72, which may, for example, serve to compress the incoming image data, while maintaining descriptive image data available for reference by server 70 and other components of the PACS 62. Where desired, server 70 and/or interface 72 may also serve to process image data accessed through the server 70. The server is also coupled to internal clients, as indicated at reference numeral 74, each client typically including a workstation at which a radiologist, physician, or clinician may access image data from the server and view or output the reconstructed image as desired. Such a reviewing workstation is discussed more below, and is an example of where aspects of the present technique may be implemented. Clients 74 may also input information, such as dictation of a radiologist following review of examination sequences. Similarly, server 70 may be coupled to one or more interfaces, such as a printer interface 76 designed to access image data and to output hard copy images via a printer 78 or other peripheral.

Server 70 may associate image data, and other workflow information within the PACS by reference to one or more database servers 80, which may include cross-referenced information regarding specific image sequences, referring or diagnosing physician information, patient information, background information, work list cross-references, and so forth. The information within database server 80, such as a DICOM database server, serves to facilitate storage and association of the image data files with one another, and to allow requesting clients to rapidly and accurately access image data files stored within the system.

Similarly, server 70 is coupled to one or more archives 82, such as an optical storage system, which serve as repositories of large volumes of image data for backup and archiving purposes. Techniques for transferring image data between server 70, and any memory associated with server 70 forming a short term storage system, and archive 82, may follow any suitable data management scheme, such as to archive image data following review and dictation by a radiologist, or after a sufficient time has lapsed since the receipt or review of the image files. An archive 82 system may be designed to receive and process image data, and to make the image data available for review.

Additional systems may be linked to the PACS, such as directly to server 70, or through interfaces such as interface 72. In the embodiment illustrated in FIG. 1, a radiology department information system or RIS 84 is linked to server 70 to facilitate exchanges of data, typically cross-referencing data within database server 80, and a central or departmental information system or database. Similarly, a hospital information system or HIS 86 may be coupled to server 70 to similarly exchange database information, workflow information, and so forth. Where desired, such systems may be interfaced through data exchange software, or may be partially or fully integrated with the PACS system to provide access to data between the PACS database and radiology department or hospital databases, or to provide a single cross-referencing database. Similarly, external clients, as designated at reference numeral 88, may be interfaced with the PACS to enable images to be viewed at remote locations. Again, links to such external clients may be made through any suitable connection, such as wide area networks, virtual private networks, and so forth. Such external clients may employ a variety of interfaces, such as computers or workstations, to process and review image data retrieved from the PACS 62.

Similarly, the one or more clients 74 may comprise a diagnostic workstation to enable a user to access and manipulate images from one or more of the imaging systems either directly (not shown) or via the file server 70. These reviewing workstations (e.g., at client 74) at which a radiologist, physician, or clinician may access and view image data from the server 70 typically include a computer monitor, a keyboard, as well as other input devices, such as a mouse. The reviewing workstation enables the client to view and manipulate data from a plurality of imaging systems, such as MRI systems, CT systems, PET systems, and ultrasound systems.

Figure 5:
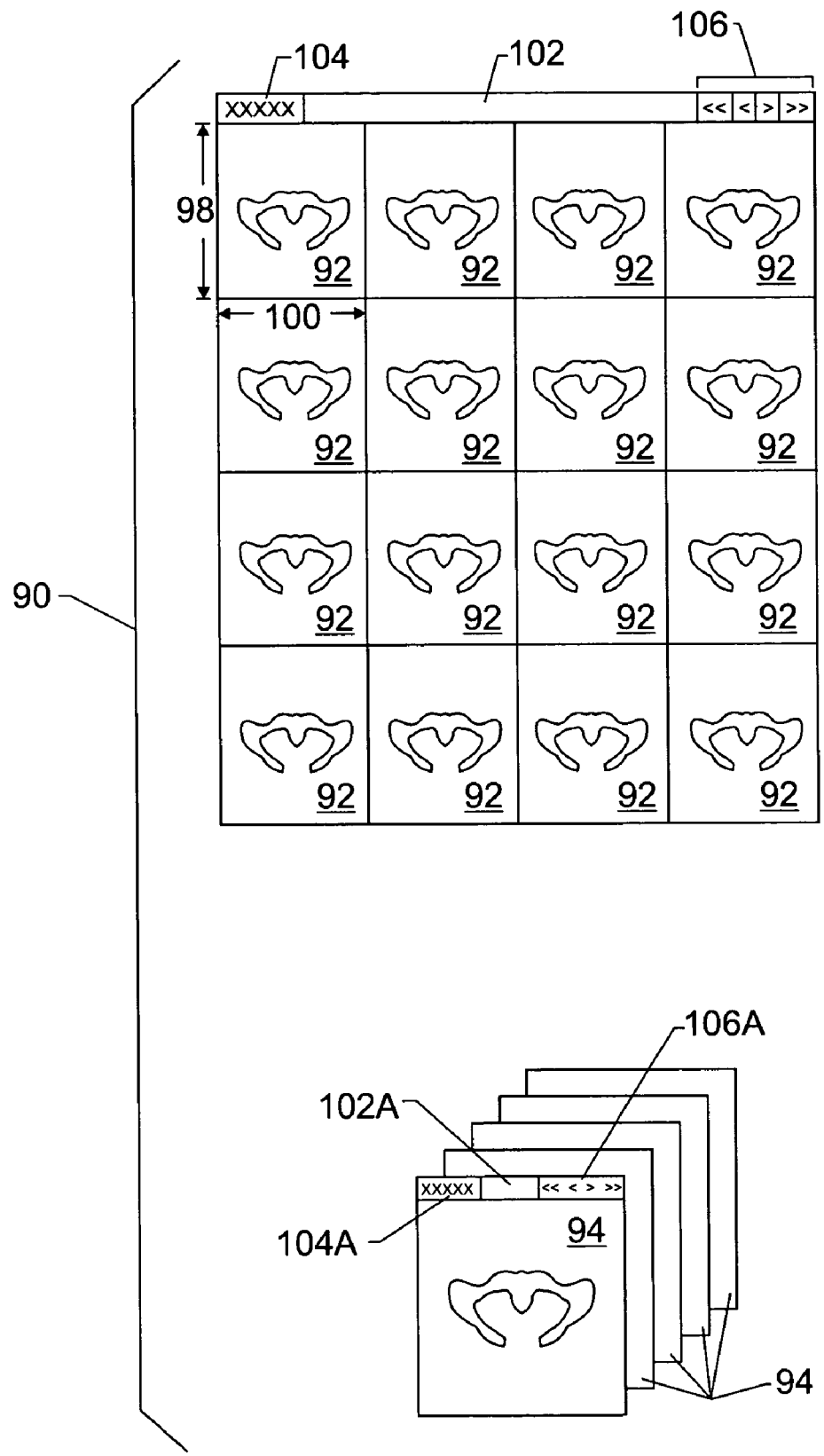
FIG. 5 is a diagrammatical representation of exemplary digitized images in sheet mode contrasted with digital images in stack mode, both types displayed via an exemplary PACS interface.

FIG. 5 illustrates a diagrammatical representation of exemplary views 90 of two series of images displayed on a PACS workstation monitor. The first series is digitized images 92 in "sheet mode" scanned from conventional sheet film. The second is digitally-acquired images 94 (digital images) displayed as an overlay in stack mode. The exemplary images are of a pelvic region 96 of a patient and, in this example, are two series of related images having a height 98 and width 100 that may be adjustable or scalable via the PACS workstation. The dimensions are more likely adjustable with PACS tools available with the digital images 94 but not available with digitized images 92 (a digitized sheet of film-based images). Both exemplary sets of images series 92 and 94 may be displayed on one or more monitors at a PACS workstation, each display in this example, having a menu bar 102 and 102A, a patient name 104 and 104A, and user-selectable arrows 106 and 106A to page back and forth through the respective image series or image studies. The number of digitized images 92 displayed on the PACS monitor may vary depending, for example, on the properties, such as size and number of images, of the scanned sheet of film. In other words, the number of digitized images 92 displayed may vary from the sixteen images illustrated in this example. As indicated, the digitally-acquired image data of the digital images 94, in general, may be more conducive to further processing, analysis, and comparison than the related digitized images 92.

An example of how a digitized sheet of film may be electronically cut and ordered may be a computer program provided on a tangible medium, configured to separate digitized images within the digitized sheet of film. The computer program may include routines for accessing a digitized sheet of film resulting from scanning of an analog sheet of film reproduced from image data acquired with a medical imaging modality. For example, the analog sheet of film may be acquired from a magnetic resonance imaging (MRI) system, a computed tomography (CT) imaging, an X-ray imaging system, or some combination of the systems. The digitized sheet of film may have a number of digitized images. The program may also include routines for slicing and collating the digitized image with a digital template, and in some embodiments, the program may include routines for storing the collated digitized images.

The difference of review capability in digitized images versus digital images is emphasized by key differences, such as the ability with digital images to register the images, study the images in stack mode, and employ other useful tools. In contrast, digitized film typically comprises one sheet of film, resulting in a relatively rigid image data file not directly susceptible to review in stack mode and other views. Accordingly, aspects of the present technique provide for cutting the digitized sheet to make possible study of the individual digitized images in stack mode, for example, both with each other and with other digitized or digital images. Clinicians, such as radiologists and other physicians and clinicians, commonly read images in stack mode, a useful approach in evaluating change that may evolve in a series of images. Moreover, stack mode may aid a pseudo three dimensional review of the two-dimensional images, coinciding with thought processes of the reviewing clinician. Viewers may "think" in three dimensions which is easier to do with a stack of a sequence of images than with a sheet of a sequence of images.

In general, image editing in accordance with the technique crops the scanned sheet of images, removing impediments to assessment of images in stack, cine and other useful viewing modes. The images may be viewed as an overlay, side-by-side, as a cine serial display, and the like. As discussed below, a clinician may first access and display the scanned film (i.e., DICOM format). Moreover, a digital template may cut the digitized sheet automatically, especially where there is less variance amongst the stored digitized sheets of film. The technique provides a tool for electronically cutting the scanned film in a variety of ways, such as by incorporating a template, computer algorithm, masking technique, segmentation, and so forth. In one embodiment, portions of the scanned film are outlined and copied, for example, by pasting the scanned film into a template, or by laying the template on top of the scanned film. The template cuts the scanned film and may put the resulting individual images in an order matching that on the analog film or in some other desired order. Finally, the processed image data may be saved for further review and processing.

Figure 6:
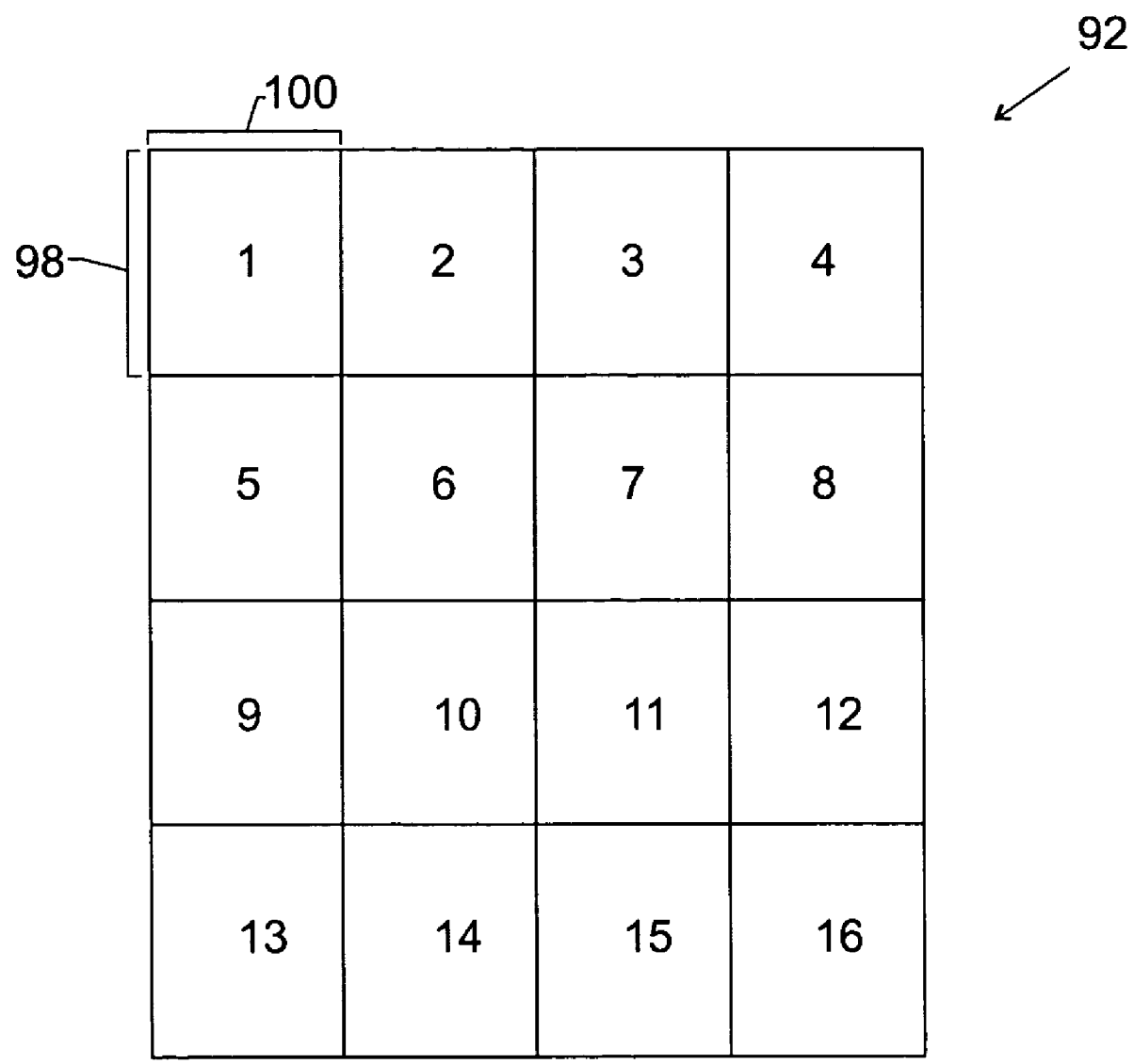
FIG. 6 is a diagrammatical representation of an exemplary template used to process digitized images scanned from a conventional analog sheet of film.

FIG. 6 is a diagrammatical representation of an exemplary template 108 used to process digitized images 92 scanned from conventional film in sheet mode. The template 108, for example, may be a graphical representation of an algorithm to "cut" and collate the digitized images 92. An image handling system, such as a PACS, may be configured to apply a predetermined template, such as the illustrated template 108, to "slice," "cut," "crop," and/or "copy" digitized images 92 scanned from sheet film. Thus, aspects of the present technique generate designated digitized images 92 cut and/or copied from digitized sheet-film-based studies. A template 108 algorithm, for example, may digitally copy pixilated image data in the selected region or regions of the digitized sheet corresponding to the selected images. The copied data may then be placed into a resulting file. This copied pixilated image data may also be added to existing digitally-acquired image data.

Figure 7:
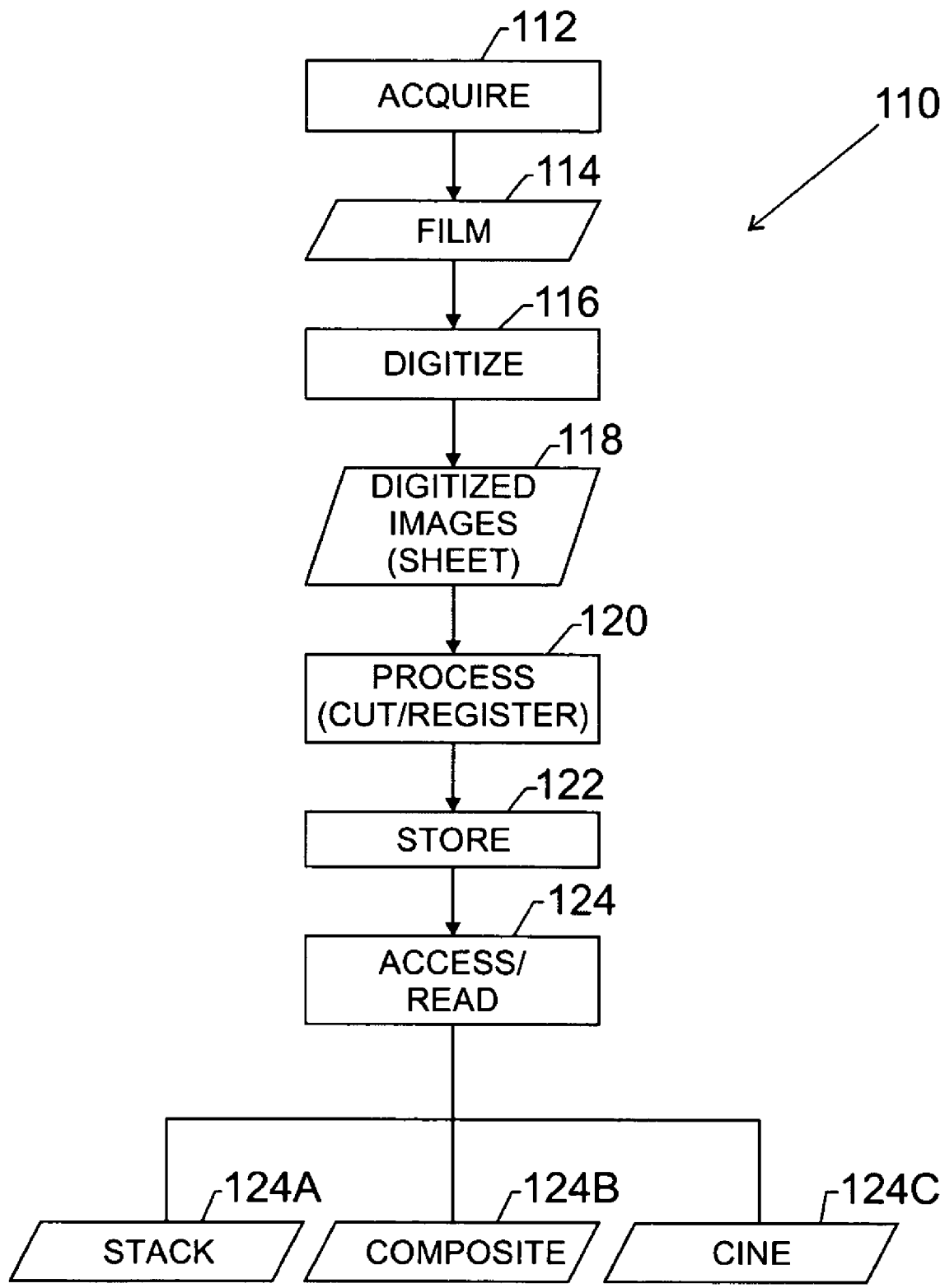
FIG. 7 is a block diagram of a method for cutting a digitized sheet of film and registering the designated images cut from the digitized sheet of film.

The technique may register these designated images and process digital sheet film-based studies for display in stack mode, and apply other functions such as linking, and ultimately result in a more effective diagnostic workflow. The technique allows the user to present and display scanned film in the same format as digitally-acquired exams and to utilize the full PACS tool set in reading scanned film studies. The PACS tool set may include, for example collating, registering, linking, composite views, side-by-side views, cine display, etc. In sum, the technique enables the user to perform more efficient and accurate diagnosis. These features may be incorporated in a variety of imaging systems and imaging handling systems, such as hospital information systems, PACS, as well as in non-medical imaging systems FIG. 7 is a block diagram of a method 110 for cutting a digitized sheet of film and registering the designated images cut and/or copied from the digitized sheet of film. Initially, the images may be acquired and processed (block 112), and reproduced on film 114. As described in FIG. 1, an imaging system generally includes some type of imager which detects signals and converts the signals to useful data. Regions of interest in a patient or other subject are thus reproduced by the imager either in a conventional support, such as photographic film, or in a digital medium. In this example, the images may be originally acquired on conventional film, such as with a conventional X-ray imaging system, or digitally-acquired originally, for example, with an MRI system or CT imaging system and then reproduced on film 114. In any case, in this embodiment, for acquisition (block 112), the images are reproduced on film 114. Ultimately, however, the film 114 is scanned to make available digitized image data, in part, because of the increasing quality and flexibility of handling and digital and digitized data. In this example, the film 114 is digitized (block 116) to produce a digitized sheet of film, such as the digitized images 92 displayed in sheet mode as illustrated in FIG. 5.

The digitized sheet 118 may then be processed (block 120) in accordance with aspects of the present technique. For example, the digitized images in sheet 118 may be cut or sliced with a template 108 or algorithm, as described above in the discussion of FIG. 6. The resulting sliced or designated images may then be collated, registered, and so forth (block 120). The processed image data, before or after registration, may be stored (block 122), for example, on a PACS system, imaging system, local or remote network, or data repository. It should be apparent that the user may decide not to store the processed image data, but instead simply read and display the processed data. In either case, the user may access, read (block 124), and display the processed data, for example, as a stack 124A, one or more composites 124B, a cine display 124C, and the like. The technique facilitates comparison of the digitized images with other digitized images and with digital images. A variety of processing and views, such as overlays, stack mode, side-by-side views, collating, and so forth, may be utilized. In sum, the technique provides a set of tools enabling the user to digitally "cut" scanned film into individual images. The technique provides a set of tools to collate and register the images, as well as, to save the images, for example, as a new DICOM series in PACS.

Figure 8:
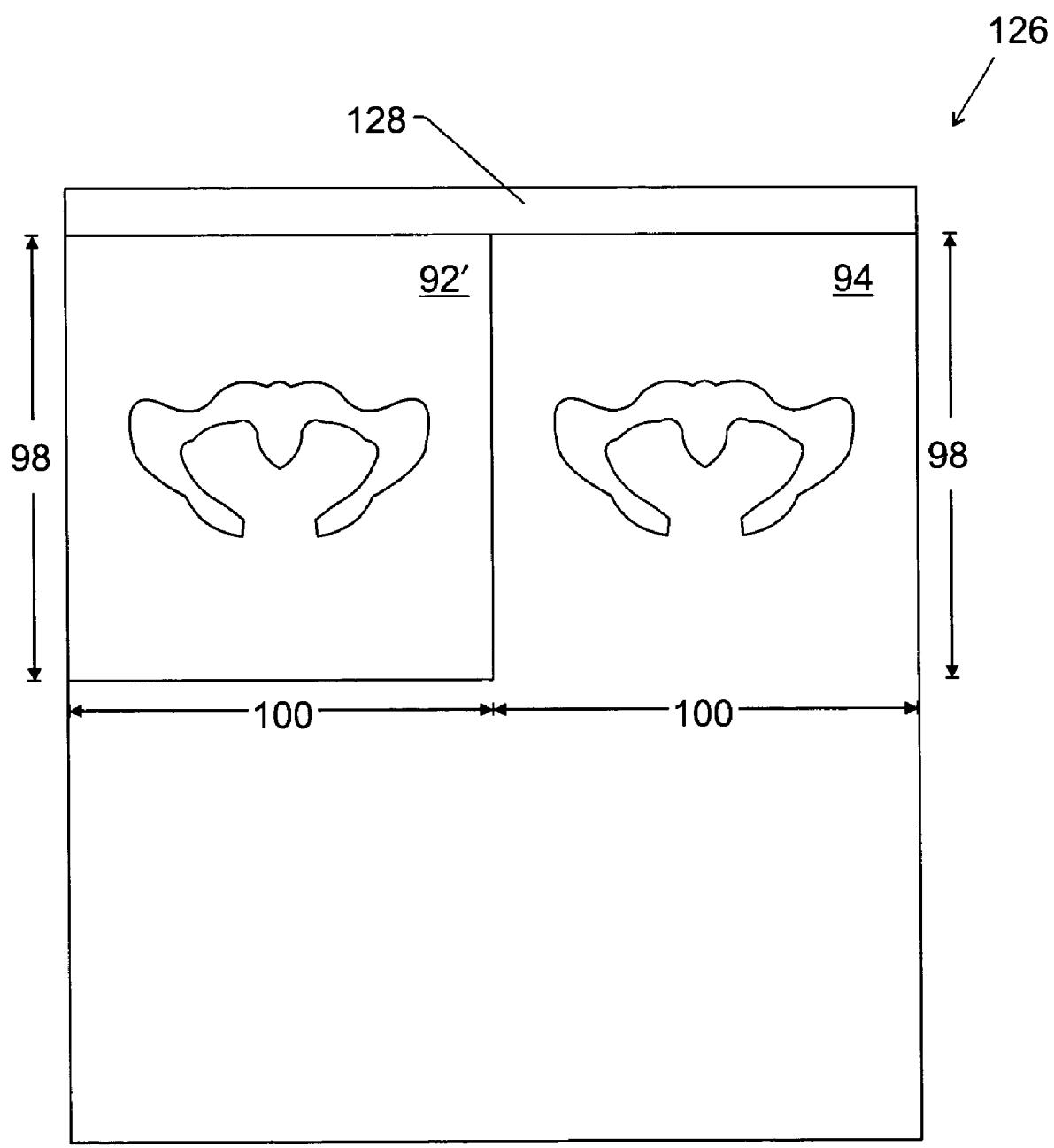
FIG. 8 is a diagrammatical representation of a PACS monitor display showing digitized images processed with the present technique compared to related digitally-acquired images.

FIG. 8 illustrates a diagrammatical representation of a PACS monitor display 126 showing images 92' processed with the present technique and compared to related digitally-acquired images 94. The PACS display 126 may have a menu bar 128 similar to that of previous figures. In this Illustrative embodiment, the processed digitized images 92' are displayed in stack mode next to the digital images 94 also displayed in stack mode. Thus, the once inflexible digitized sheet images may now be displayed in the same format as the digital images. Also, not shown, are other possible displays, including similar views, of the process digitized images 92' and the digital images 94, such as cine serial display, composite images, linked images, overlays, dispersing of the digital images with the digitized images, photo processing, and so forth. In sum, processing may include registration, for example, of the cut digitized images 92 which each other or with digital images 94. In contrast, registration and other tools in the PAC tools set, such as linking, cine, and so forth, are rendered useless on scanned films that can only be display in sheet mode, for example, on a PACS workstation, and which generally looks like a sheet of film (FIG. 5). Radiologists typically read digitally-acquired CT and MR studies in stack mode, a display format incongruent with sheet mode. The present technique addresses these different display formats and resolves this inefficient and difficult comparison of film-based (i.e., historical) sheet images with digitally-acquired image studies, permitting easy comparison of the images and potentially improving final diagnosis of the patient.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for separating digitized images on a digitized sheet of film, comprising:

accessing a digitized sheet of film having a number of images acquired discretely from one another with an medical imaging modality, the digitized sheet of film resulting from scanning of an analog sheet of film of the images, wherein the images are arranged in a regular grid on the analog sheet of film;

configuring a digital template based on the number of images and on the regular grid; and digitally slicing and collating the images on the digitized sheet by applying the digital template to the digitized sheet to provide collated digitized images corresponding to the number of images in the regular grid on the analog sheet of film.

2. The method of claim 1, wherein the digital template is configured and applied with a computer algorithm.

3. The method of claim 1, further comprising at least one of storing the collated digitized images, ordering the collated digitized images, displaying the collated digitized images in stack mode or cine mode, displaying the collated digitized images on a PACS workstation monitor, displaying the collated digitized images in combination with a DICOM header defining a series and order of the collated digitized images, registering the collated digitized images, comparing the collated digitized images with digital images, or registering the collated digitized images with digital images.

4. The method of claim 1, wherein original image data of the digitized images reproduced on the sheet of film is acquired with at least one of a magnetic resonance imaging (MRI) system, a computed tomography (CT) imaging, or an X-ray imaging system.

5. The method of claim 4, wherein the digitized sheet is stored after the sheet of film is scanned to generate the digitized sheet.

6. The method of claim 1, wherein the images comprise defined borders.

7. The method of claim 1, wherein configuring a digital template comprises configuring a digital template based on the number of images and on the regular grid, and without performing image segmentation.

8. The method of claim 1, wherein configuring a digital template comprises configuring a digital template based on the number of images and on the regular grid, and not on content of the images.

9. The method of claim 1, wherein configuring a digital template comprises partitioning the images based on the number and size of the images without interpreting content of the images.

10. The method of claim 1, wherein configuring a digital template comprises partitioning the images based on the number and size of the images without image segmentation of content of the images.

11. The method of claim 1, wherein configuring a digital template comprises configuring a digital template based on dimensions of the images on the analog sheet of film.

12. The method of claim 1, wherein configuring a digital template comprises configuring a digital template based on dimensions of the regular grid.

13. The method of claim 1, wherein digitally slicing and collating the images comprises separating and collating the images on the digitized sheet by applying the digital template to the digitized sheet without performing image segmentation.

14. The method of claim 1, wherein digitally slicing via the digital template comprises outlining the images and copying image data of each image to respective image files.

15. A system for separating digitized images within an image file of a digitized sheet of film, comprising:
  means for accessing a digitized sheet of film having a number of digitized images, the sheet of film resulting from scanning of an analog sheet of film reproduced from images separately acquired with a medical imaging modality, the analog sheet of film having a number of image frames having substantially the same dimensions and corresponding to the number of digitized images;
  means for configuring a digital template based on the number and dimensions of the image frames to partition the image frames;
  means for digitally slicing and collating the digitized images with the digital template;
  means for storing the collated digitized images; and
  wherein the images are originally reproduced on the analog sheet of film from image data acquired with at least one of a magnetic resonance imaging (MRI) system, a computed tomography (CT) imaging, or an X-ray imaging system.

16. The system of claim 15, further comprising means for displaying the collated digitized images on a PACS workstation monitor in stack mode or cine mode.

17. The system of claim 15, further comprising means for ordering and registering the collated digitized images.

18. The system of claim 15, wherein each of the digitized images comprise borders defined by one or more of the number or the dimensions of each of the digitized images.

19. The system of claim 18, wherein the means for configuring a digital template is based on the borders of the digitized images, and without performing image segmentation.

20. The system of claim 15, wherein the means for configuring a digital template is based on the number and dimensions of the image frames, and not on the content of the digitized images.

21. The system of claim 15, wherein the means for configuring a digital template is based on the number and dimensions of the image frames without interpreting content of the images.

22. The system of claim 15, wherein the means for configuring a digital template comprises a means for partitioning the image frames, and wherein the image frames are partitioned without image segmentation of content of the images.

23. The system of claim 15, wherein the means for configuring a digital template comprise a means for configuring a digital template based on the dimensions of the images on the analog sheet of film.

24. The system of claim 15, wherein a configuration of the digitized images on the digitized sheet of film is a substantially regular pattern.

25. The system of claim 24, wherein the means for configuring a digital template is based on the substantially regular pattern.

26. The system of claim 24, wherein the substantially regular pattern comprises borders corresponding to edges of the digitized images.

27. The system of claim 26, wherein the means for configuring a digital template comprises a means for partitioning the image frames along the borders.

28. The system of claim 15, wherein the means for digitally slicing and collating the digitized images comprises a means for separating and collating the digitized images on the digitized sheet of film by applying the digital template to the digitized sheet of film without performing image segmentation.

29. The system of claim 15, wherein the means for digitally slicing comprises a means for outlining the digitized images and copy respective image data to respective files.

30. A computer program, provided on a computer-readable medium for separating digitized images within an image file of a digitized sheet of film, comprising:
  a routine for accessing a digitized sheet of film having a number of images, the sheet of film resulting from scanning of an analog sheet of film reproduced from image data acquired with a medical imaging modality, wherein the images are discretely acquired and arranged in a regular array on the analog sheet of film;
  a routine for configuring a digital template correlative to the number of images and the regular array;

a routine for digitally slicing and collating the digitized images with the digital template;

a routine for storing the collated digitized images; and wherein the discrete images are originally reproduced on the analog sheet of film from image data acquired with at least one of a magnetic resonance imaging (MRI) system, a computed tomography (CT) imaging, and an X-ray imaging system.

31. The computer program on a computer-readable medium of claim 30, further comprising a routine for displaying the collated digitized images on a PACS workstation monitor in stack mode or cine mode.

32. The computer program on a computer-readable medium of claim 30, further comprising a routine for ordering and registering the collated digitized images.

* * * * *

UNITED STATES PATENT AND TRADEMARK OFFICE
CERTIFICATE OF CORRECTION

PATENT NO. : 7,574,030 B2  Page 1 of 1
APPLICATION NO. : 10/723790
DATED : August 11, 2009
INVENTOR(S) : Fors et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1479 days.

Signed and Sealed this

Seventh Day of September, 2010

David J. Kappos
*Director of the United States Patent and Trademark Office*